United States Patent
Wang et al.

(10) Patent No.: US 12,253,506 B2
(45) Date of Patent: Mar. 18, 2025

(54) METHOD OF ANOMALY DETECTION, METHOD OF BUILDING UPSTREAM-AND-DOWNSTREAM CONFIGURATION, AND MANAGEMENT SYSTEM OF SENSORS

(71) Applicant: INDUSTRIAL TECHNOLOGY RESEARCH INSTITUTE, Hsinchu (TW)

(72) Inventors: Yu-Lin Wang, Tainan (TW); Guang-Huei Gu, Tainan (TW); Chih-Jen Chen, Tainan (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 210 days.

(21) Appl. No.: 17/969,641

(22) Filed: Oct. 19, 2022

(65) Prior Publication Data
US 2024/0027416 A1  Jan. 25, 2024

(30) Foreign Application Priority Data
Jul. 20, 2022  (TW) .................................. 111127135

(51) Int. Cl.
    *G01N 33/00* (2006.01)
    *G01N 33/18* (2006.01)
(52) U.S. Cl.
    CPC ......... *G01N 33/0075* (2013.01); *G01N 33/18* (2013.01)
(58) Field of Classification Search
    CPC .... G01N 33/0075; G01N 33/18; G06Q 10/20; G06F 16/2228; G06F 16/2462
    See application file for complete search history.

(56) References Cited

U.S. PATENT DOCUMENTS

| 9,959,374 B2 | 5/2018 | Rosti |
| 10,543,741 B2 | 1/2020 | Biderman et al. |

(Continued)

FOREIGN PATENT DOCUMENTS

| CN | 105181898 | 12/2015 |
| CN | 105283876 A | 1/2016 |

(Continued)

OTHER PUBLICATIONS

Taiwan Office Action dated Mar. 9, 2023 as received in application No. 111127135.

(Continued)

*Primary Examiner* — Quan Zhen Wang
*Assistant Examiner* — Mancil Littlejohn, Jr.
(74) *Attorney, Agent, or Firm* — Maschoff Brennan

(57) ABSTRACT

A method of building upstream-and-downstream configuration of sensors includes determining two sets of geographic position data of a target sensor and a candidate sensor, obtaining pollution-associated periods according to pieces of flow field data, the sets of geographic position data and pieces of target sensing data of the target sensor to determine a pollution-associated period, calculating a correlation between target sensing data obtained by the target sensor during the pollution-associated period and candidate sensing data obtained by the candidate sensor during the associated air pollution period to obtain sensor correlations, and determining the target sensor and the candidate sensor having a upstream-and-downstream relationship with the candidate sensor being used as a satellite sensor of the target sensor when a quantity ratio of sensor correlations being larger than or equal to a correlation threshold is larger than or equal to a default ratio.

17 Claims, 11 Drawing Sheets

(56) References Cited

U.S. PATENT DOCUMENTS

| | | |
|---|---|---|
| 10,648,805 B2 | 5/2020 | Bai |
| 10,690,562 B2 | 6/2020 | Rieker |
| 10,775,258 B2 | 9/2020 | Muralidhar |
| 10,890,350 B2 | 1/2021 | Martin |
| 2011/0251800 A1 | 10/2011 | Wilkins |
| 2018/0313649 A1 | 11/2018 | Bai |

FOREIGN PATENT DOCUMENTS

| | | |
|---|---|---|
| CN | 112131739 | 12/2020 |
| TW | 201835784 A | 10/2018 |
| TW | 1640963 | 11/2018 |
| TW | 698760 | 7/2020 |
| TW | M598942 | 7/2020 |
| TW | M605632 | 12/2020 |
| TW | I720324 | 3/2021 |

OTHER PUBLICATIONS

Punsompong, "Identification of potential sources of PM10 pollution from biomass burning in northern Thailand using statistical analysis of trajectories" 2018.

Luo, "Potential Sources and Transport Pathways of PM2.5 in Shanghai, China" Jul. 2020.

Lin "Using trajectory model and weather patterns to investigate PM2.5 potential source areas of Taichung City" Retreived Sep. 12, 2022.

Yan "A heavy haze episode in Beijing in Feb. 2014 characteristics, origins and implications" 2015.

METHOD OF ANOMALY DETECTION, METHOD OF BUILDING UPSTREAM-AND-DOWNSTREAM CONFIGURATION, AND MANAGEMENT SYSTEM OF SENSORS

CROSS-REFERENCE TO RELATED APPLICATIONS

This non-provisional application claims priority under 35 U.S.C. § 119(a) on Patent Application No(s). 111127135 filed in Republic of China (ROC) on Jul. 20, 2022, the entire contents of which are hereby incorporated by reference.

BACKGROUND

1. Technical Field

This disclosure relates to a management method of sensors, more particularly, to a method of building upstream-and-downstream configuration and method of anomaly detection of sensors.

2. Related Art

Water quality sensor and air quality sensor are common sensors. The water quality sensor can be used to sense data such as the concentration of phosphate and hydrogen sulfide in water, and the air quality sensor can be used to sense air data such as carbon dioxide concentration and suspended particulate concentration. Take the air quality sensor as an example, a large number of air quality sensors are installed in many fields (for example, offshore wind power generation areas) and spread in wide area to monitor the air quality in the field. However, in the event of installing a large number of air quality sensors, it costs a large amount of resource to perform regular inspections and irregular maintenance operations on these air quality sensors, which increases time, labor and money. In addition, most of the regular inspections use a random inspection method on the sensors, which is not only inefficient, but may even miss some malfunction sensors.

SUMMARY

Accordingly, this disclosure provides a method of building upstream-and-downstream configuration, method of anomaly detection and management system of sensors.

According to an embodiment of the disclosure, a method of building upstream-and-downstream configuration of sensor, performed by a computing device, includes: obtaining two pieces of geographic location data of a target sensor and a candidate sensor; determining at least one pollution-associated period according to a number of pieces of flow field data corresponding to different time, the two pieces of geographic location data and a plurality of pieces of target sensing data obtained by the target sensor; for each of the at least one pollution-associated period, calculating a correlation between the pieces of target sensing data obtained during the pollution-associated period and a plurality of pieces of candidate sensing data obtained during the pollution-associated period by the candidate sensor to obtain a number of sensor correlations corresponding to the pollution-associated period; and when a quantity ratio of sensor correlation being greater than or equal to a correlation threshold among the sensor correlations is greater than or equal to a default ratio, determining the candidate sensor has an upstream-and-downstream relationship with the target sensor, and storing upstream-and-downstream relationship information corresponding to the candidate sensor and the target sensor, wherein the upstream-and-downstream relationship information indicates the candidate sensor being a satellite sensor of the target sensor.

According to an embodiment of the disclosure, a method of anomaly detection of sensors, performed by a computing device, includes: obtaining an upstream-and-downstream configuration table of a target sensor, wherein the upstream-and-downstream configuration table records the target sensor having upstream-and-downstream relationships with a number of satellite sensors; for each of the satellite sensors, performing a pollution determination algorithm according to a number of pieces of detection flow field data, a number of pieces of geographic location data and a number of pieces of detection sensing data of the target sensor, to determine whether at least one detection pollution period exists, and when determining the at least one detection pollution period exists, performing: for each of the at least one detection pollution period, calculating a correlation between a number of pieces of target detection data obtained by the target sensor in the detection pollution period and a number of pieces of satellite detection data obtained by the satellite sensor in the detection pollution period to obtain a number of detection correlations, setting a settlement result as 1 when a quantity ratio of detection correlation being greater than or equal to a correlation threshold among the detection correlations is less than a default ratio, and setting a settlement result as 0 when the quantity ratio of detection correlation being greater than or equal to the correlation threshold among the detection correlations is greater than or equal to the default ratio; calculating an error ratio according to the settlement results of the satellite sensors and a total number of the corresponding satellite sensors; and outputting an anomaly notification associated with the target sensor when the error ratio is greater than or equal to an error threshold.

According to an embodiment of the disclosure, a management system for sensors includes: a storage device storing a number of pieces of target sensing data obtained by a target sensor, a number of pieces of candidate sensing data obtained by a candidate sensor and two pieces of geographic location data of the target sensor and the candidate sensor; and a computing device electrically connected to the storage device, and configured to perform a building upstream-and-downstream configuration procedure, which includes: determining at least one pollution-associated period according to a number of pieces of flow field data, the two pieces of geographic location data and the pieces of target sensing data obtained by the target sensor; for each of the at least one pollution-associated period, calculating a correlation between a number of pieces of target sensing data obtained by the target sensor during the pollution-associated period and a number of pieces of candidate sensing data obtained by the candidate sensor during the pollution-associated period to obtain a number of sensor correlations; and determining the candidate sensor has an upstream-and-downstream relationship with the target sensor when a quantity ratio of sensor correlation being greater than or equal to a correlation threshold among the sensor correlations is greater than or equal to a default ratio, and storing upstream-and-downstream relationship information corresponding to the candidate sensor and the target sensor, wherein the upstream-and-downstream relationship information indicates the candidate sensor being a satellite sensor of the target sensor.

DETAILED DESCRIPTION

In the following detailed description, for purposes of explanation, numerous specific details are set forth in order to provide a thorough understanding of the disclosed embodiments. According to the description, claims and the drawings disclosed in the specification, one skilled in the art may easily understand the concepts and features of the invention. The following embodiments further illustrate various aspects of the invention, but are not meant to limit the scope of the invention.

Figure 1:
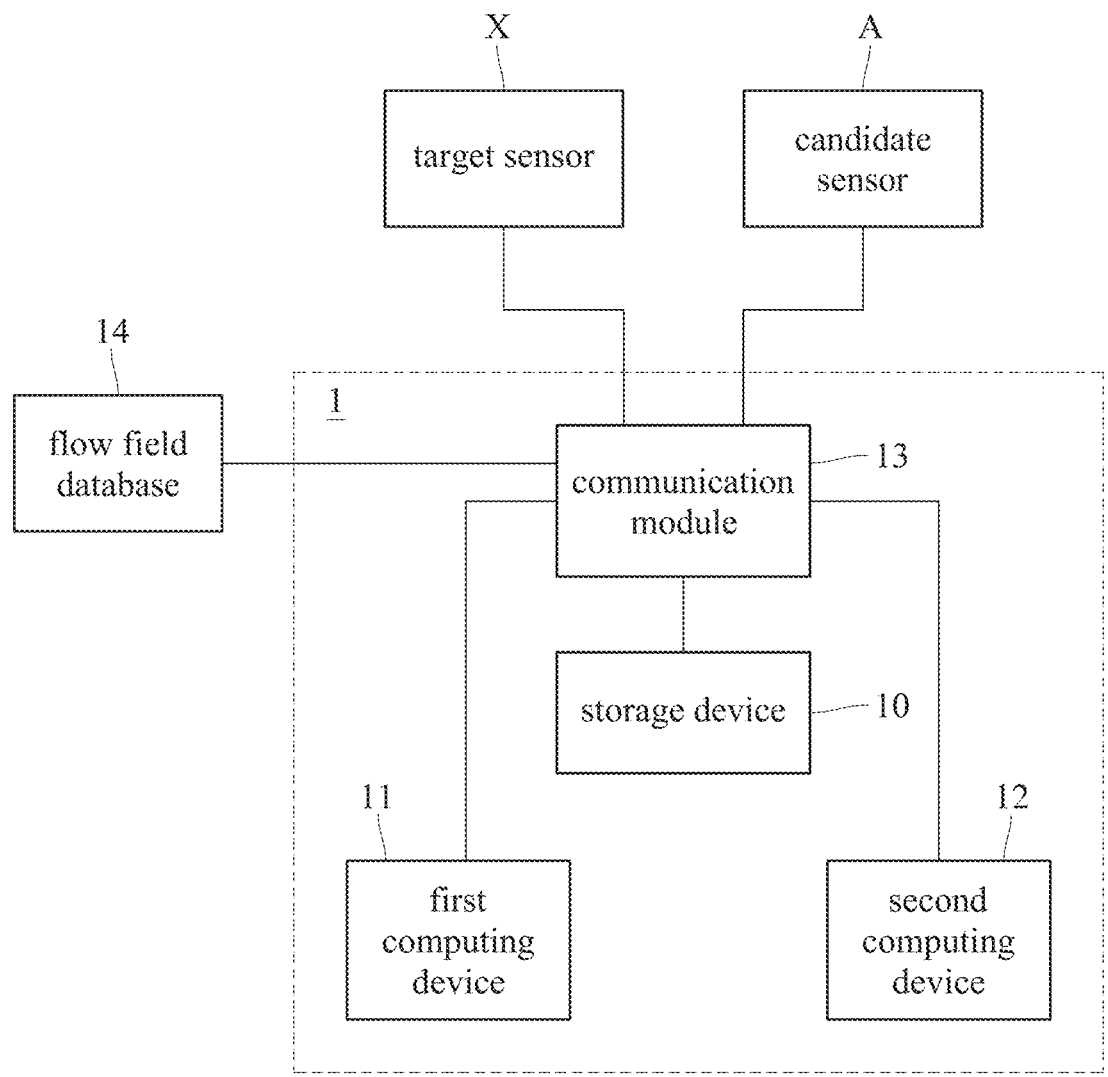
FIG. 1 is a block diagram illustrating a management system for sensors, a target sensor and a candidate sensor according to an embodiment of the disclosure.

Please refer to FIG. 1, wherein FIG. 1 is a block diagram illustrating a management system 1 for sensors, a target sensor and a candidate sensor according to an embodiment of the disclosure. For example, the management system 1 for sensors may manage a number of sensors with air quality sensing functions (such as the target sensor X and the candidate sensor A shown in FIG. 1) in specific industrial areas and offshore wind power generation areas, may also manage a number of sensors with water quality sensing functions. (such as the target sensor X and the candidate sensor A shown in FIG. 1) on seashores and rivers, for example, computing upstream-and-downstream relationship between sensors and building upstream-and-downstream configuration, and detecting sensor operations etc. As shown in FIG. 1, the management system 1 for sensors includes a storage device 10, a first computing device 11 and a second computing device 12, wherein the first computing device 11 and the second computing device 12 are electrically connected to the storage device 10. Further, the first computing device 11 and the second computing device 12 may also be connected to the storage device 10 in a wireless way. For example, the management system 1 may include a communication module 13, wherein the communication module 13 may be connected to the target sensor X, the candidate sensor A, the storage device 10, the first computing device 11 and the second computing device 12 in a wired or wireless way. In addition, if the storage device 10, the first computing device 11 and the second computing device 12 themselves already have communication elements, the communication module 13 may be an element selectively disposed.

The storage device 10 may include, but not limited to, a flash memory, a hard drive (HDD), a solid state drive (SSD), a dynamic random-access memory (DRAM) or a static random-access memory (SRAM). The storage device 10 may store geographic location information of the target sensor X and the candidate sensor A, a number of pieces of target sensing data generated by the target sensor X for previously performed sensing, a number of pieces of candidate sensing data generated by the candidate sensor A for previously performed sensing, and upstream-and-downstream relationship information of the target sensor X, wherein the upstream-and-downstream relationship information indicates that the candidate sensor A generating the candidate sensing data associated with the target sensing data in a certain time period is a satellite sensor of the target sensor X. In an implementation where the target sensor X and the candidate sensor A are sensors for sensing air quality, the target sensing data and the candidate sensing data may include concentration values of one or more of ozone ($O_3$), fine suspended particles ($PM_{2.5}$), suspended particles ($PM_{10}$), carbon monoxide (CO), carbon dioxide ($SO_2$) and nitrogen dioxide ($NO_2$). In an implementation where the target sensor X and the candidate sensor A are sensors for sensing water quality, the target sensing data and the candidate sensing data may include concentration values of one or more of turbidity, pH, nitrite, dissolved oxygen, Phosphate and hydrogen sulfide.

The first computing device 11 and the second computing device 12 may each include, but not limited to, a single processor and integration of multiple microprocessors, such as central processing unit (CPU), graphics processing unit (GPU), etc. The first computing device 11 may be connected to a flow field database 14 through the communication module 13, and obtain a number of pieces of flow field data at the location the target sensor X according to the geographic location information of the target sensor X. Said flow field database 14 may include weather database or water flow field database. The weather database or water flow field database stores the flow field data corresponding to different locations and time. Therefore, the pieces of flow field data may be obtained from the weather database or water flow field database, wherein the flow field data may be a number of pieces of wind field data or a number of pieces of water flow field data. The first computing device 11 may determine whether an upstream-and-downstream relationship exists between the target sensor X and the candidate sensor A according to the geographic location information of the target sensor X and the candidate sensor A, the pieces of target sensing data obtained by the target sensor X, the pieces of target sensing data obtained by the candidate sensor A and the pieces of flow field data. Further, the first computing device 11 may store the upstream-and-downstream relationship information into the storage device 10 when the upstream-and-downstream relationship exists between the target sensor X and the candidate sensor A. The upstream-and-downstream relationship information indicates that the candidate sensor A is the satellite sensor of the target sensor X.

The second computing device 12 may perform anomaly detection on the target sensor X according to the upstream-and-downstream relationship information corresponding to the target sensor X, wherein the details of anomaly detection are described below. Specifically, the first computing device 11 may be a computing device owned by a supplier of an air quality sensor or a water quality sensor. The second computing device 12 may be a computing device owned the buyers or users of the air quality sensor or the water quality sensor, and may be installed with management application program provided by the supplier of the air quality sensor or the water quality sensor.

The communication module 13 may include one or more of a Bluetooth module, an EnOcean module, WiFi module, ZigBee module, 2G module, 3G module, 4G module, 5G module and radio frequency identification (RFID) module, the disclosure is not limited thereto. The communication module 13 may be used to transmit sensing data of the target sensor X and the candidate sensor A to the storage device 10 and/or the first computing device 11 and/or the second computing device 12. In addition, the communication module 13 may be used for the first computing device 11 and the second computing device 12 to obtain data from external database, wherein said external database is, for example, the flow field database 14.

In some embodiments, the first computing device and the second computing device may be integrated into a single computing device, meaning functions of the two computing devices are realized by one computing device, and examples are given below. In another embodiment, the management system for sensors is similar to the previous embodiment, which includes the communication module 13, the storage device 10 and the first computing device 11, but the management system for sensors of this embodiment does not include the second computing device. In this embodiment, the first computing device 11 may perform function of building the upstream-and-downstream relationship between the target sensor X and the satellite sensor as well as function of the anomaly detection on the target sensor X. In still another embodiment, the target sensor X and the candidate sensor A are included in the sensor system. It should be noted that, FIG. 1 exemplarily illustrates one target sensor X and one candidate sensor A, but a number of the target sensors and the candidate sensors manageable by the management system for sensors is not limited thereto.

Figure 2:
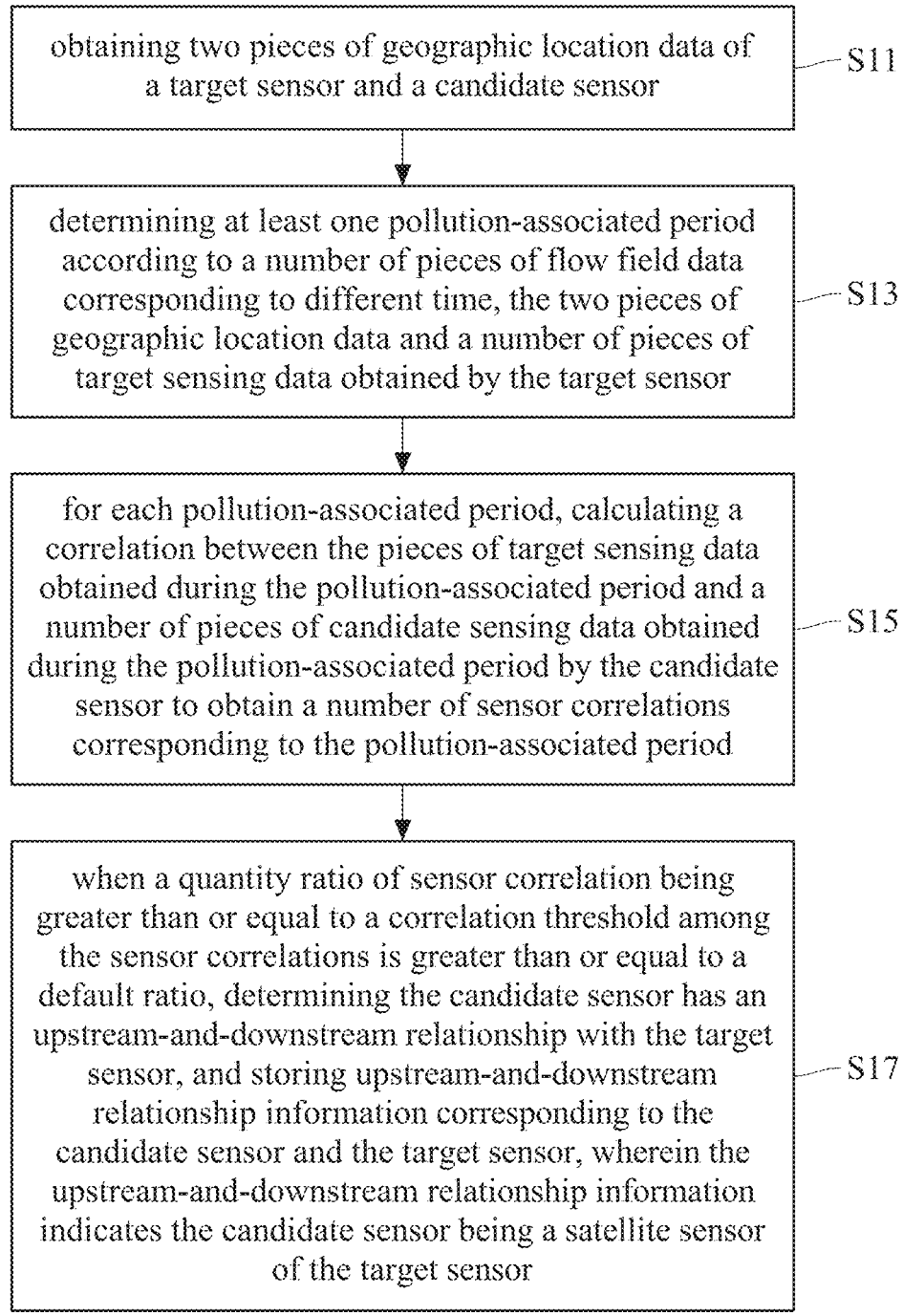
FIG. 2 is a flowchart illustrating the method of building upstream-and-downstream configuration for sensors according to an embodiment of the disclosure.
Figure 3A:
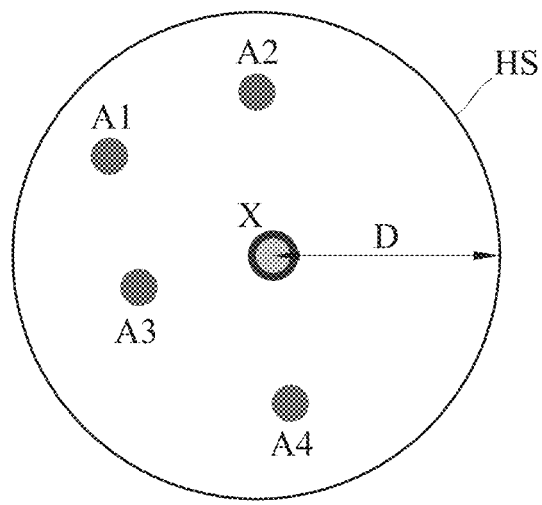
FIG. 3a to FIG. 3c are schematic diagrams illustrating performing the method of building upstream-and-downstream configuration for sensors according to an embodiment of the disclosure.
Figure 3B:
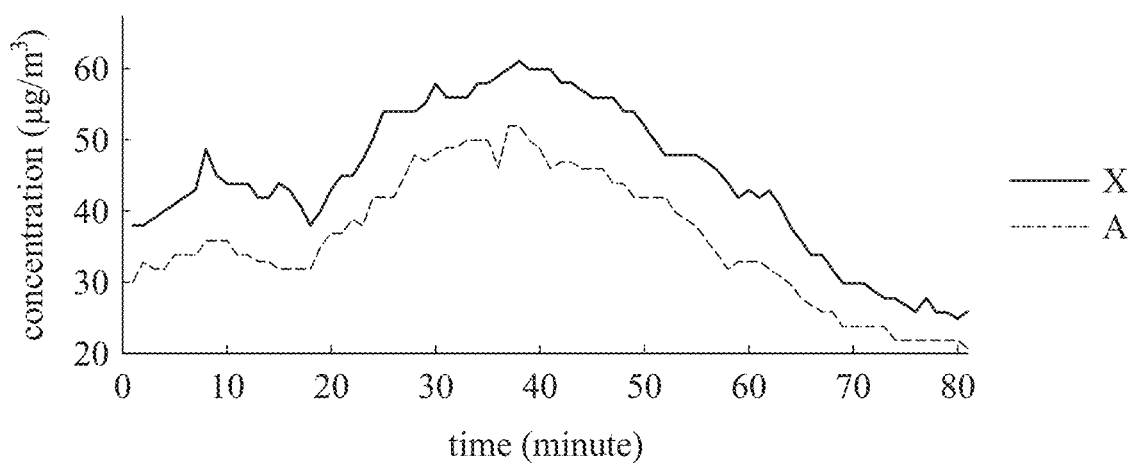
Figure 3C:
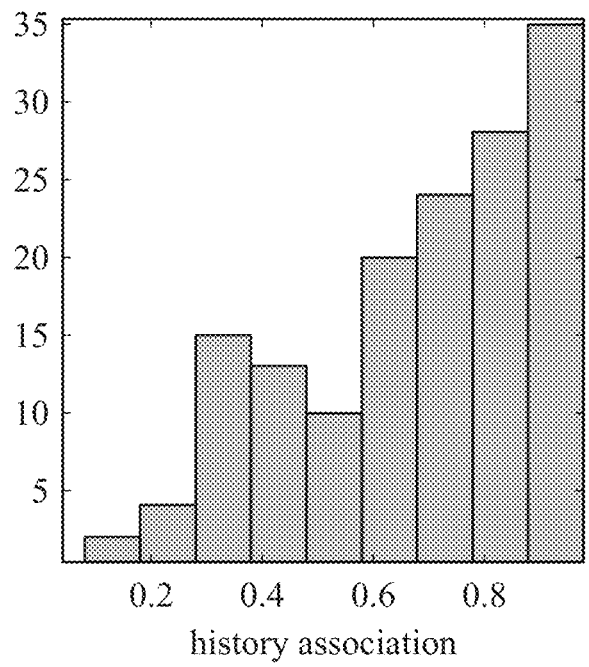

The following describes the method of building upstream-and-downstream configuration for sensors of the present application along with FIG. 1, FIG. 2 and FIGS. 3a to 3c, wherein FIG. 2 is a flowchart illustrating the method of building upstream-and-downstream configuration for sensors according to an embodiment of the disclosure, and FIG. 3a to FIG. 3c are schematic diagrams illustrating performing the method of building upstream-and-downstream configuration for sensors according to an embodiment of the disclosure. The method of building upstream-and-downstream configuration for sensors and schematic diagrams of performing thereof shown in FIG. 2 and FIGS. 3a to 3c are adapted to the management system 1 for sensors shown in FIG. 1, especially to the communication module 13, the storage device 10 and the first computing device 11 of the management system 1 for sensors, but is not limited thereto.

As shown in FIG. 2, the method of building upstream-and-downstream configuration for sensors may include, by the computing device, performing: step S11, obtaining two pieces of geographic location data of a target sensor and a candidate sensor; step S13, determining at least one pollution-associated period according to a number of pieces of flow field data corresponding to different time, the two pieces of geographic location data and a number of pieces of target sensing data obtained by the target sensor; step S15, for each pollution-associated period, calculating a correlation between the pieces of target sensing data obtained during the pollution-associated period and a plurality of pieces of candidate sensing data obtained during the pollution-associated period by the candidate sensor to obtain a number of sensor correlations corresponding to the pollution-associated period; and step S17, when a quantity ratio of sensor correlation being greater than or equal to a correlation threshold among the sensor correlations is greater than or equal to a default ratio, determining the candidate sensor has an upstream-and-downstream relationship with the target sensor, and storing upstream-and-downstream relationship information corresponding to the candidate sensor and the target sensor, wherein the upstream-and-downstream relationship information indicates the candidate sensor being a satellite sensor of the target sensor.

Specifically, take FIG. 3a as an example, after selecting the target sensor X, the first computing device 11 may determine, according to the geographic location information of the target sensor X, each of the hot zone sensors A1-A4 with a distance to the target sensor X being smaller than a distance threshold D as the candidate sensor, wherein the distance threshold D is, for example, 5 km, but is not limited thereto. For example, multiple hot zone sensors A1-A4 may locate in the hot zone HS with a radius being the distance threshold D, and the first computing device 11 may use the hot zone sensors A1-A4 one by one as the candidate sensor A for performing the following steps, thereby determining whether each of the candidate sensors is the satellite sensor of the target sensor X, or may select one of the hot zone sensors A1-A4 as the candidate sensor A to perform the determination.

In step S11, the first computing device 11 obtains the geographic location data of each of the target sensor X and the candidate sensor A from the storage device 10, wherein the geographic location data may be in two-dimensional coordinates form or in longitude and latitude form, the disclosure is not limited thereto.

In step S13, the first computing device 11 obtains the pieces of flow field data from the weather database or water flow field database through the communication module 13 according to the geographic location information of the target sensor X, and determines one or more pollution-associated periods according to the two pieces of geographic location data of the target sensor X and the candidate sensor A and the pieces of target sensing data obtained by the target sensor X in the past from the storage device 10, wherein the pollution-associated period refers to the period in which pollution (pollution event) has occurred according to the target sensing data obtained by the target sensor X in the past. The pollution-associated period may refer to a period where one pollution event has occurred or a collection of periods where multiple pollution events have occurred. Details of step S13 are described later.

In step S15, for each pollution-associated period, the first computing device 11 calculates the correlations between the pieces of target sensing data obtained by the target sensor X and the candidate sensing data obtained by the candidate sensor A to obtain a number of sensor correlations corresponding to the pollution-associated periods. Please refer to FIG. 3b, wherein FIG. 3b exemplarily illustrates air pollution data obtained by the target sensor X and the candidate sensor A for one pollution-associated period, wherein the solid line represents the target sensing data obtained by the target sensor X, and the dotted line represents the candidate sensing data obtained by the candidate sensor A. The first computing device 11 may calculate a correlation coefficient between the target sensing data and the candidate sensing data during the pollution-associated period, and use the correlation coefficient as the sensor correlation corresponding to the pollution-associated period. The correlation coefficient is, especially, a coefficient of determination (represented by $R^2$). In a case where there are multiple pollution-associated periods, the first computing device 11 performs step S15 for multiple times based on different pollution-associated periods to obtain a number of sensor correlations corresponding to the pollution-associated periods.

In step S17, the first computing device 11 may determine, among the sensor correlations corresponding to all of the pollution-associated periods, whether a quantity ratio of the sensor correlations being larger than or equal to the correlation threshold is larger than or equal to a default ratio, to determine whether an upstream-and-downstream relationship exists between the target sensor X and the candidate sensor A. In detail, the first computing device 11 may count the number of the sensor correlations, to calculate the number of the sensor correlations within each value range. For example, if the sensor correlation of the pollution-associated period shown in FIG. 3b (such as the coefficient of determination of data of the dotted line and data of the solid line) is 0.9636, the first computing device 11 may add one count to the sensor correlation of 0.9 in FIG. 3c. When the quantity ratio for the sensor correlation reaching (greater than or equal to) the correlation threshold is larger than or equal to the default ratio, the first computing device 11 determines that the candidate sensor A and the target sensor X have the upstream-and-downstream relationship; and when the quantity ratio for the sensor correlations being larger than or equal to the correlation threshold is not larger than or equal to the default ratio, the first computing device 11 determines that the candidate sensor A and the target sensor X do not have an upstream-and-downstream relationship. For example, the correlation threshold is 0.6, the default ratio is 50%. In this example, the first computing device 11 may determine whether a ratio of a number of the sensor correlations among the sensor correlations being larger than or equal to 0.6 to a number of all sensor correlations is larger than or equal to 50%. The first computing device 11 determines the upstream-and-downstream relationship exists between the target sensor X and the candidate sensor A when the quantity ratio is larger than or equal to 50%, and stores the upstream-and-downstream relationship information of the target sensor X and the candidate sensor A into the storage device 10, wherein the upstream-and-downstream relationship information indicates the candidate sensor A may be the satellite sensor of the target sensor X. In addition, the first computing device 11 may further include an upstream-and-downstream configuration table corresponding to the target sensor X. The upstream-and-downstream configuration table is used to record the upstream-and-downstream relationship information, and includes an identification number of the target sensor X and an identification number of the satellite sensor of the target sensor X. In other embodiments, the upstream-and-downstream configuration table may also be stored in the storage device 10, and the first computing device 11 builds and updates the upstream-and-downstream configuration table stored in the storage device 10. Moreover, each candidate sensor may be used as the target sensor to perform the method of building upstream-and-downstream configuration for sensors to have a respective upstream-and-downstream configuration table, and the first computing device 11 and/or the storage device 10 may store the upstream-and-downstream configuration table corresponding to each sensor.

Figure 4:
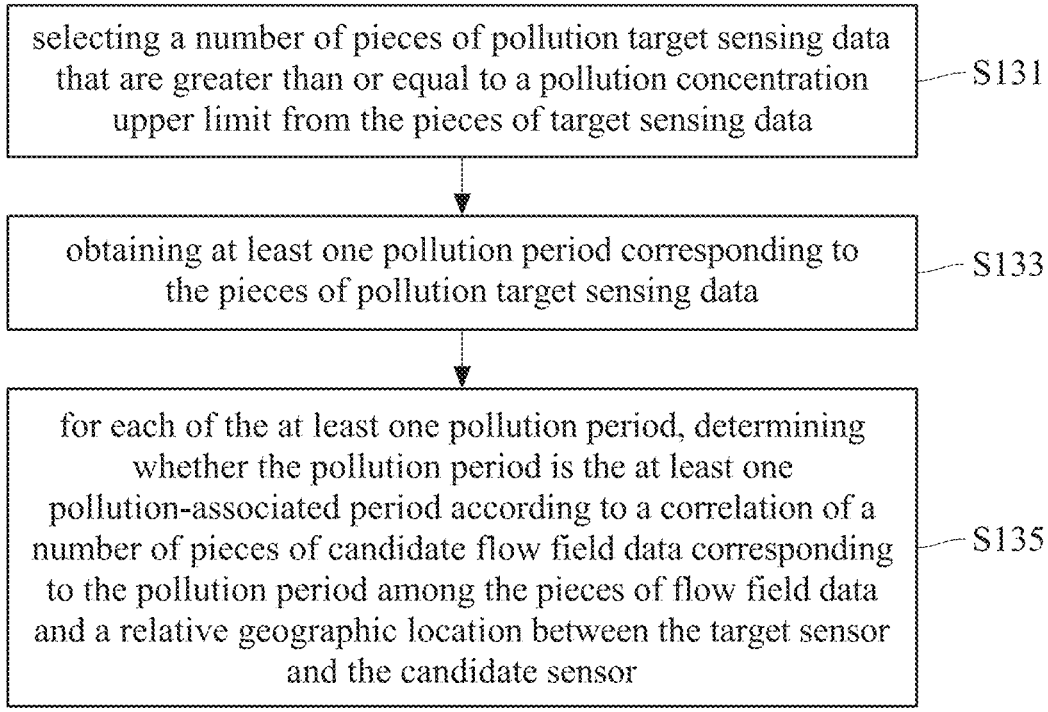
FIG. 4 is a flowchart illustrating obtaining a pollution-associated period in the method of building upstream-and-downstream configuration for sensors according to an embodiment of the disclosure.

Please refer to FIG. 1 and FIG. 4 for further explanation of step S13 in FIG. 2, wherein FIG. 4 is a flowchart illustrating obtaining a pollution-associated period in the method of building upstream-and-downstream configuration for sensors according to an embodiment of the disclosure. The steps shown in FIG. 4 describe performing a pollution determination algorithm according to a pollution concentration upper limit, wherein the pollution concentration upper limit indicates the maximum allowable concentration of specific gases (such as harmful gases) or specific substances (such as harmful substances) in air or water, and for example, the pollution concentration upper limit may be pre-stored in the first computing device 11, but is not limited thereto, and may be stored in the storage device 10. As shown in FIG. 4, in step S13 of FIG. 2, the first computing device 11 performs one pollution determination algorithm to determine one or more pollution-associated periods, and the pollution determination algorithm may include: step S131, selecting a number of pieces of pollution target sensing data that are greater than or equal to a pollution concentration upper limit from the pieces of target sensing data; step S133, obtaining at least one pollution period corresponding to the pieces of pollution target sensing data; and step S135, for each of the at least one pollution period, determining whether the pollution period is the at least one pollution-associated period according to a correlation of a number of pieces of candidate flow field data corresponding to the pollution period among the pieces of flow field data and a relative geographic location between the target sensor and the candidate sensor.

In step S131, the first computing device 11 selects a number of pieces of pollution target sensing data from the pieces of target sensing data of the target sensor X stored in the storage device 10, wherein the selected pieces of pollution target sensing data are larger than or equal to the pollution concentration upper limit. In step S133, the first computing device 11 obtains the at least one pollution period corresponding to the pollution target sensing data. The pollution period may refer to a period when one piece of pollution target sensing data is generated, or a collection of multiple periods when a number of pieces of pollution target sensing data are generated respectively.

The first computing device 11 performs step S135 on each of the pollution periods respectively, and the following further describes step S135 in detail. In step S135, the first computing device 11 obtains a number of pieces of candidate flow field data among the pieces of flow field data corresponding to the target sensor X from the weather database or water flow field database, wherein the obtained pieces of candidate flow field data correspond to the pollution period. The first computing device 11 computes the relative geographic location between the target sensor X and the candidate sensor A. In the present embodiment, the relative geographic location between the target sensor X and the candidate sensor A is a connection direction between the target sensor X and the candidate sensor A. The first computing device 11 determines an included angle between a flow field direction of each of the pieces of candidate flow field data and the connection direction between the target sensor X and the candidate sensor A, determines whether the included angle is smaller than or equal to an angle tolerance, and uses the pollution period as one of the pollution-associated periods, wherein the used pollution period corresponds to the candidate flow field data associated with the included angle being smaller than or equal to the angle tolerance. The candidate flow field data is, for example, an average value of the wind field data obtained during the corresponding pollution period.

Figure 5:
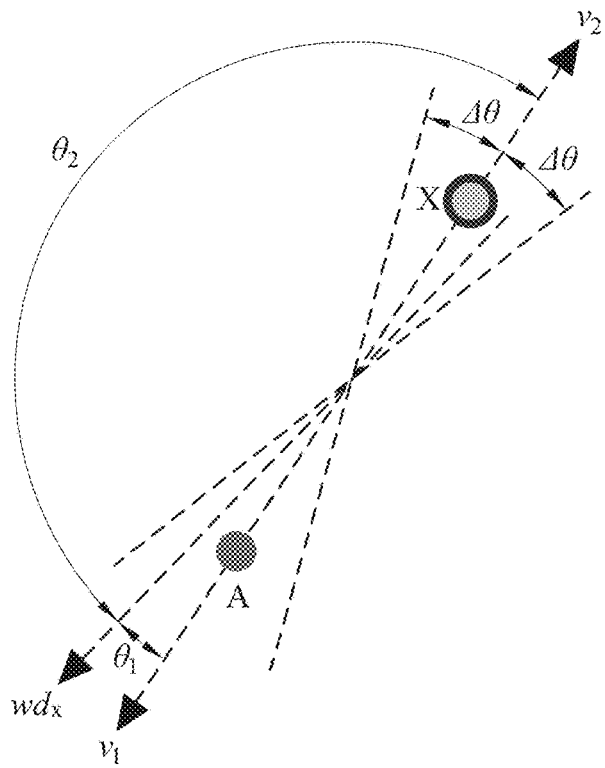
FIG. 5 is a schematic diagram exemplarily illustrating determining a relative geographic location between the two sensors.

The following describes method of calculating the relative geographic location between the target sensor X and the candidate sensor A in more detail. In the present embodiment, the relative geographic location is the connection direction between the target sensor X and the candidate sensor A. Please refer to FIG. 5, which is a schematic diagram exemplarily illustrating determining the relative geographic location between the two sensors. In the implementation of FIG. 5, the first computing device 11 reads the geographic location data of the target sensor X and the geographic location data of the candidate sensor A from the storage device 10, and computes the relative geographic location between the target sensor X and the candidate sensor A according to the two pieces of geographic location data, meaning the connection direction between the target sensor X and the candidate sensor A.

Moreover, the first computing device 11 performs computation to obtain a first direction $v_1$ from the target sensor X to the candidate sensor A, and to obtain a second direction $v_2$ from the candidate sensor A to the target sensor X. A difference between the first direction $v_1$ and the second direction $v_2$ is 180°, and the relative geographic location of the target sensor X and the candidate sensor A is represented by the first direction $v_1$ and the second direction $v_2$. In step S135, after the first computing device 11 obtains the relative geographic location between the target sensor X and the candidate sensor A (i.e. after obtaining the first direction $v_1$ and the second direction $v_2$), the first computing device 11 further computes a correlation between the relative geographic location and the pieces of candidate flow field data. The first computing device 11 computes the included angle between each one of the pieces of candidate flow field data and the first direction $v_1$, and the included angle between each one the pieces of candidate flow field data and the second direction $v_2$. FIG. 5 shows the candidate flow field data $wd_x$ as an example for description, the candidate flow field data $wd_x$ represents the direction of the flow field. The first computing device 11 obtains the included angle $\theta_1$ between the candidate flow field data $wd_x$ and the first direction $v_1$, and the included angle $\theta_2$ between the candidate flow field data $wd_x$ and the second direction $v_2$.

Then, the first computing device 11 determines whether the included angle $\theta_1$ or $\theta_2$ is smaller than or equal to the angle tolerance, and when determining any one of the included angle $\theta_1$ or $\theta_2$ is smaller than or equal to the angle tolerance, the first computing device 11 uses the pollution period corresponding to the candidate flow field data associated with this included angle as one of the pollution-associated periods. The candidate flow field data is, for example, an average value of wind field data obtained in the corresponding pollution period, meaning an average direction or a mean vector of the wind field directions. In the embodiment, the correlation between the relative geographic location and the pieces of candidate flow field data is the included angle $\theta_1$, $\theta_2$.

Figure 6:
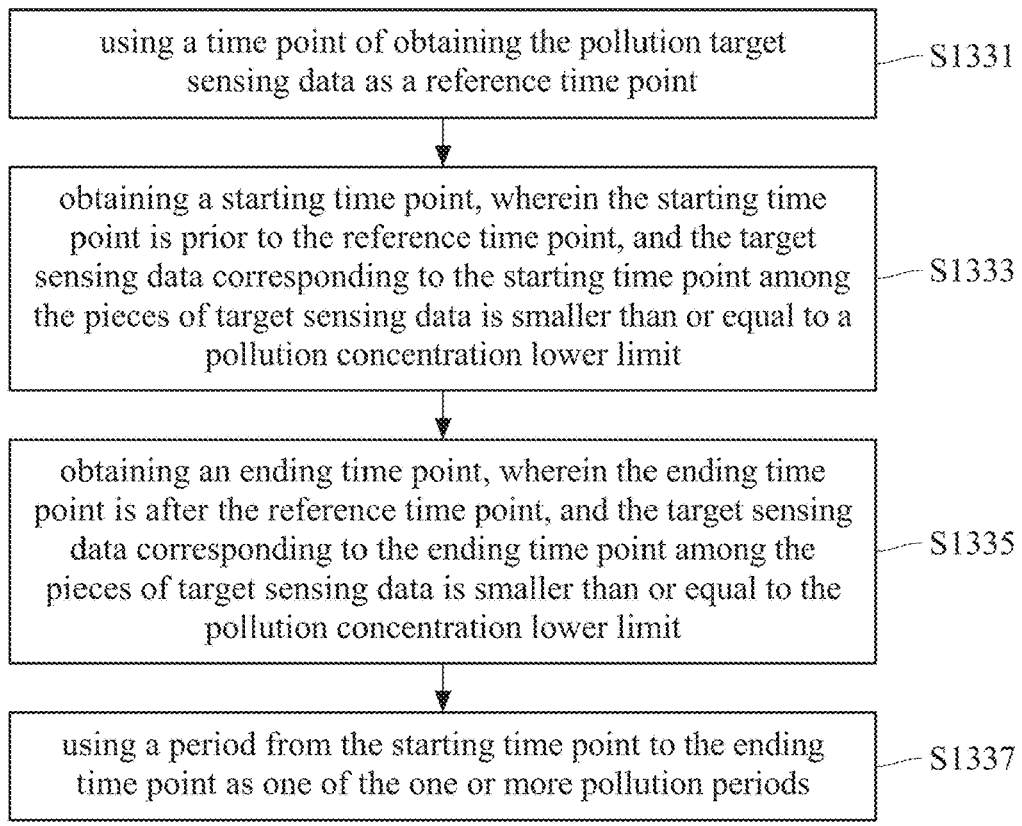
FIG. 6 is a flowchart illustrating obtaining a pollution period in the method of building upstream-and-downstream configuration for sensors according to an embodiment of the disclosure.
Figure 7:
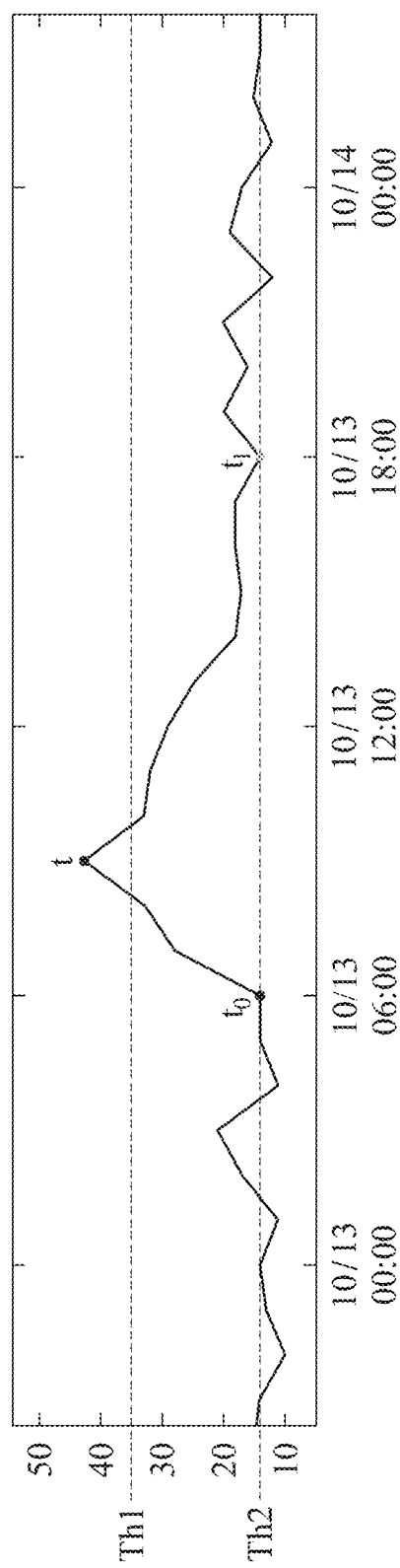
FIG. 7 is a schematic diagram illustrating performing obtaining a pollution period in the method of building upstream-and-downstream configuration for sensors according to an embodiment of the disclosure.

To further describe embodiments of obtaining one or more pollution periods corresponding to the pollution target sensing data, please refer to FIG. 1, FIG. 6 and FIG. 7, wherein FIG. 6 and FIG. 7 are a flowchart and a schematic diagram illustrating obtaining a pollution period in the method of building upstream-and-downstream configuration for sensors according to an embodiment of the disclosure, respectively.

As shown in FIG. 6, step S133 of FIG. 4 may include, for each of the pieces of pollution target sensing data, performing: step S1331, using a time point of obtaining the pollution target sensing data as a reference time point; step S1333, obtaining a starting time point, wherein the starting time point is prior to the reference time point, and the target sensing data corresponding to the starting time point among the pieces of target sensing data is smaller than or equal to a pollution concentration lower limit; step S1335, obtaining an ending time point, wherein the ending time point is after the reference time point, and the target sensing data corresponding to the ending time point among the pieces of target sensing data is smaller than or equal to the pollution concentration lower limit; and step S1337, using a period from the starting time point to the ending time point as one of the one or more pollution periods. It should be noted that, FIG. 6 illustrates step S1333 to be performed before step S1335, but step S1333 may also be performed after step S1335, or may be performed simultaneously with step S1335.

In step S1331, the first computing device 11 determines the target sensing data reaching the pollution concentration upper limit Th1, uses this piece of target sensing data as the pollution target sensing data, and uses the time point of generating the pollution target sensing data as the reference time point t. In step S1333, the first computing device 11 obtains the starting time point $t_0$ that is prior to the reference time point t, and the target sensing data corresponding to the starting time point $t_0$ among the pieces of target sensing data is smaller than or equal to the pollution concentration lower limit Th2. In other words, among a number of time points corresponding to the pieces of target sensing data being smaller than or equal to the pollution concentration lower limit Th2 obtained prior to the reference time point t, the time point that is the closest to the reference time point t is the starting time point $t_0$. Similarly, in step S1335, the first computing device 11 obtains the ending time point $t_1$ after the reference time point t, and the target sensing data corresponding to the ending time point $t_1$ among the pieces of target sensing data is smaller than or equal to the pollution concentration lower limit Th2. In other words, in a number of time points corresponding to the pieces of target sensing data being smaller than or equal to the pollution concentration lower limit Th2 and is obtained after the reference time point t, the time point that is the closest to the reference time point is the ending time point $t_1$. In step S1337, the first computing device 11 may use a period from the starting time point $t_0$ to the ending time point $t_1$ as one pollution period. For example, the pollution concentration upper limit Th1 may be set as 35 μg/m$^3$, and the pollution concentration lower limit Th2 may be set as 15 μg/m$^3$.

Figure 8:
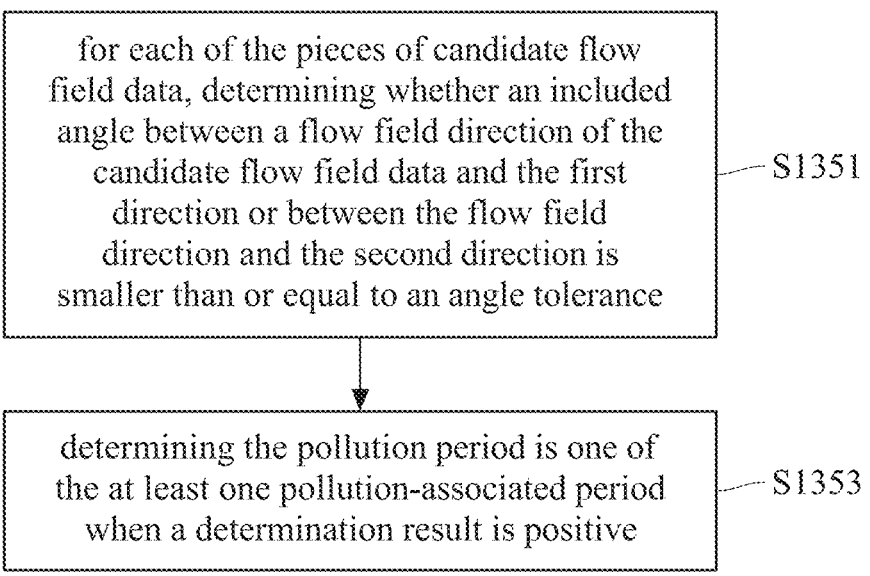
FIG. 8 is a flowchart illustrating selecting a pollution-associated period in the method of building upstream-and-downstream configuration for sensors according to an embodiment of the disclosure.

To further describe the embodiment of selecting the pollution-associated period from the pollution periods (step S135 of FIG. 4), please refer to FIG. 1 and FIG. 8, wherein FIG. 8 is a flowchart illustrating selecting a pollution-associated period in the method of building upstream-and-downstream configuration for sensors according to an embodiment of the disclosure.

As shown in FIG. 8, step S135 of FIG. 4 may include: step S1351, for each of the pieces of candidate flow field data, determining whether an included angle between a flow field direction of the candidate flow field data and the first direction or between the flow field direction and the second direction is smaller than or equal to an angle tolerance; and step S1353, determining the pollution period is one of the at least one pollution-associated period when a determination result is positive. In step S1353, the positive determination result indicates that the included angle between at least one of the first direction or the second direction and the flow field direction is smaller than or equal to the angle tolerance.

In other words, take FIG. 5 as an example, the first computing device 11 may rotate the first direction $v_1$ with the angle tolerance $\Delta\theta$ along clockwise and counterclockwise directions respectively as boundaries of a first angle range; and similarly, the first computing device 11 may rotate the second direction $v_2$ with the angle tolerance $\Delta\theta$ along clockwise and counterclockwise directions respectively as boundaries of a second angle range, and the above-mentioned positive determination result indicates the flow field direction falling within the first angle range or the second angle range. Specifically, positive determination result for the first angle range may be represented as the following inequality (1), and positive determination result for the second angle range may be represented as the following inequality (2):

$$v_1-\Delta\theta < wd < v_1+\Delta\theta \quad \text{inequality (1)}$$

$$v_2-\Delta\theta < wd < v_2+\Delta\theta \quad \text{inequality (2)}$$

wherein $\Delta\theta$ is, for example, 20°, and wd is the flow field direction.

Therefore, when determining the included angle between the flow field direction in the candidate flow field data corresponding to the pollution period and the first direction or the second direction is smaller than or equal to the angle tolerance (the flow field direction falling within the first direction range or the second direction range), the pollution period may be used as the pollution-associated period. That is, the target sensor X and the candidate sensor A may have an upstream-and-downstream relationship during the pollution period, and the target sensing data and the candidate sensing data obtained during the period may be used to calculate the correlation between the target sensor X and the candidate sensor A, to thereby determining whether an upstream-and-downstream relationship exists between the target sensor X and the candidate sensor A.

Figure 9:
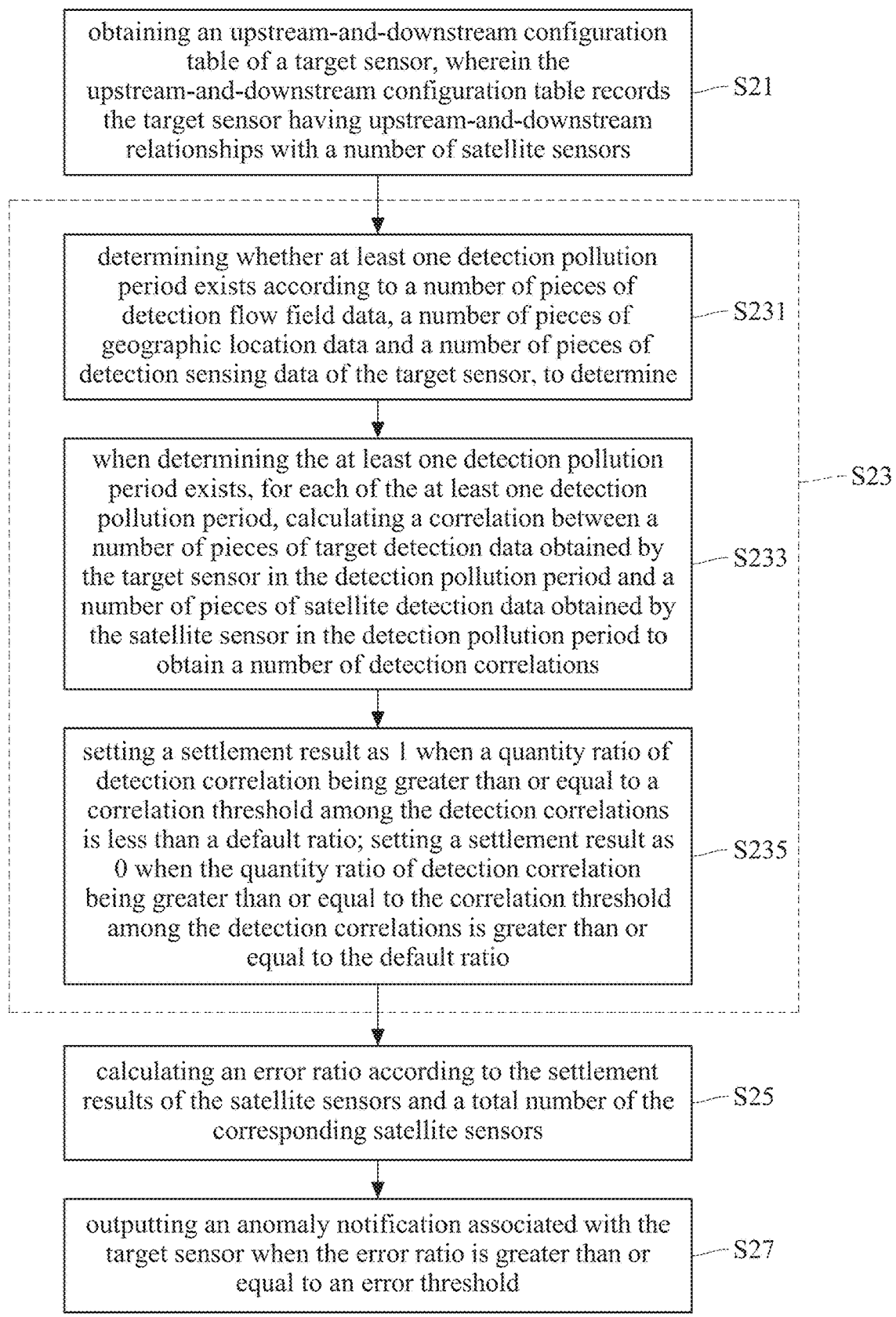
FIG. 9 is a flowchart illustrating method of anomaly detection of sensors according to an embodiment of the disclosure.

Please refer to FIG. 1 and FIG. 9, wherein FIG. 9 is a flowchart illustrating method of anomaly detection of sensors according to an embodiment of the disclosure.

As shown in FIG. 9, the method of anomaly detection of sensors may include, by the second computing device 12, performing: step S21, obtaining an upstream-and-downstream configuration table of a target sensor, wherein the upstream-and-downstream configuration table records the target sensor having upstream-and-downstream relationships with a number of satellite sensors. The upstream-and-downstream configuration table may be obtained by the first computing device 11 performing steps S11, S13, S15 and S17 in advance on each of the candidate sensors one by one to determine a number of satellite sensors of the target sensor, and to record the result into the upstream-and-downstream configuration table. Then, the second computing device 12 performs step S23 on each of the satellite sensors, which includes performing steps S231, S233 and S235 to obtain a settlement result of each satellite sensor. The second computing device 12 performs step S25 to calculate an error ratio according to the settlement result of the satellite sensors and a total number of the corresponding satellite sensors. The second computing device 12 performs step S27 to output an anomaly notification associated with the target sensor when the error ratio reaches an error threshold.

Moreover, in step S23, each of the satellite sensors is performed with: step S231, performing a pollution determination algorithm according to a number of pieces of detection flow field data, a number of pieces of geographic location data and a number of pieces of detection sensing data of the target sensor, to determine whether at least one detection pollution period exists; step S233, when the at least one detection pollution period is determined, for each of the at least one detection pollution period, calculating a correlation between a number of pieces of target detection data obtained by the target sensor in the detection pollution period and a number of pieces of satellite detection data obtained by the satellite sensor in the detection pollution period to obtain a number of detection correlations; and step S235, setting a settlement result as 1 when a quantity ratio of detection correlation being greater than or equal to a correlation threshold among the detection correlations is less than to a default ratio; setting a settlement result as 0 when the quantity ratio of detection correlation being greater than or equal to the correlation threshold among the detection correlations is greater than or equal to the default ratio. It should be noted that, the flow field data described in the method of building upstream-and-downstream configuration for sensors is history data, and may be different from the detection flow field data described in the method of anomaly detection of sensors, wherein the detection flow field data may also be obtained by the first computing device 11 from the flow field database 14.

In particular, in the management system 1 including two computing devices shown in FIG. 1, the upstream-and-downstream configuration table of the target sensor may be created by the first computing device 11, and steps S21-S27 are performed by the second computing device 12. As for the management system including single computing device, the building of upstream-and-downstream configuration table of the target sensor and steps S21-S27 are performed by the same computing device. It should be noted that, steps S23-S27 may be performed periodically (for example, performed each month). For example, steps S23-S27 may be performed based on the flow field data and sensing data of each sensor of each month after building the upstream-and-downstream relationship information.

Steps S231, S233, S235 shown in FIG. 9 are performed on each satellite sensor one by one. In step S231, the detection flow field data indicates the flow field direction at the target sensor X during the detection candidate period, the detection sensing data indicates data obtained by the target sensor X during the detection candidate period, wherein the detection candidate period is obtained by a method similar to that of the pollution-associated period in step S135 of FIG. 4. In detail, in step S231, at least one pollution period is obtained according to data obtained by the target sensor X being greater than or equal to the pollution concentration upper limit, and the flow field data (such as the flow field direction) corresponding to each pollution period is obtained. Then, the following is performed on each satellite sensor: obtaining the relative geographic location between the satellite sensor and the target sensor X, such as the connection direction of the satellite sensor and the target sensor X, and calculating the included angle between the connection direction and the flow field data of each pollution period (which may be referred to FIG. 5, wherein the sensor A may be analogous to any satellite sensor of the present embodiment); when the included angle is smaller than or equal to the angle tolerance, using the pollution period associated with this included angle as the detection pollution period of the satellite sensor; and determining that the detection pollution period corresponding to the satellite sensor exists.

In step S233 of FIG. 9, when the result of step S231 is that the at least one detection pollution period exits, for each detection pollution period, the following is performed: calculating a correlation between a number of pieces of target detection data obtained by the target sensor X during the detection pollution period and a number of pieces of satellite detection data obtained by the satellite sensor during the detection pollution period to obtain a number of detection correlations. The target detection data in step S233 refers to all pieces of sensing data obtained by the target sensor X during the detection pollution period, the satellite detection data refers to all pieces of sensing data obtained by the satellite sensor during the detection pollution period, and the detection correlation refers to a correlation between sensing data obtained by the target sensor X during the detection candidate periods and sensing data obtained by the satellite sensor during the detection candidate periods.

For better understanding, the following uses the operation of the second computing device 12 to describe steps in FIG. 8. After obtaining the detection correlations, in step S235, the second computing device 12 calculates the quantity ratio of detection correlation among the detection correlations reaching the correlation threshold, and counts the quantity of detection correlations to determine whether the quantity ratio of the detection correlation falling in each value range reaches the default ratio, to thereby setting the settlement result. Moreover, the detection correlation may be implemented with the correlation coefficient (such as correlation of determination). Similar to step S17 of FIG. 2, the second computing device 12 may add one count to the value range corresponding to the detection correlation. After finishing counting all of the detection correlations, the second computing device 12 may determine a total number of the detection correlations, among all detection correlations, reaching the correlation threshold. When the quantity ratio of the detection correlations reaching the correlation threshold reaches the default ratio, the second computing device 12 sets the settlement result corresponding to the satellite sensor as 0; and when the quantity ratio of the detection correlation reaching the correlation threshold does not reach the default ratio, the second computing device 12 sets the settlement result corresponding to the satellite sensor as 1. In particular, values of the correlation threshold and the default ratio used in step S235 are the same as the correlation threshold and the default ratio used for building the upstream-and-downstream relationship as described above, respectively, such as 0.6 and 50%.

As described above, step S23 is performed on each satellite sensor. Therefore, the second computing device 12 may obtain the settlement result corresponding to the satellite sensor. In particular, the second computing device 12 may record the settlement result corresponding to the satellite sensor into a table. In step S25, the second computing device 12 calculates the error ratio according to the settlement result of each satellite sensor and a total number of the corresponding satellite sensors, especially by dividing a sum of the settlement results of the sensors by the total number of the satellite sensors, and multiplying with the percentage (100%).

Then, in step S27, the second computing device 12 determines whether the error ratio reaches the error threshold to determine whether to output the anomaly notification associated with the target sensor X, wherein the error threshold is, for example, 50%. When the error ratio reaches the error threshold, it means that the correlation between the sensing data of the target sensor X and the sensing data of the satellite sensor does not meet the corresponding standard, and that there may be abnormal condition happened at the target sensor X. Therefore, the second computing device 12 may output the anomaly notification associated with the target sensor X to a monitor station for sensors. On the other hand, when the error ratio does not reach the error threshold, it means that the target sensor X is normal.

Moreover, the second computing device 12 may perform steps S23-S27 periodically (for example, every month) to determine whether the target sensor X functions normally, and record the settlement result as the detection result table. For example, the second computing device 12 may only record the newest settlement result to the detection result table (as shown in table 1). That is, the second computing device 12 may overwrite the previous detection result with the newest settlement result. The second computing device 12 may also record the settlement result of each detection to the detection result table. Table 1 exemplarily presents results of performing three detections on the four satellite sensors of the target sensor X, and only the result of the third detection is presented (i.e. the newest detection result), but the number of satellite sensors as well as the number of times of performing detection are not limited thereto. The value of the settlement result corresponding to the first satellite sensor represents the detection result between the first satellite sensor and the target sensor X, and values of the settlement results corresponding to other satellite sensors also represents the same meaning. Moreover, value "0" represents the detection result being that the quantity ratio of the detection correlation of the satellite sensor reaching the correlation threshold reaches the default ratio; and value "1" represents the detection result being that the quantity ratio of the detection correlation of the satellite sensor reaching the correlation threshold does not reach the default ratio, wherein the calculation of the detection correlation is described above and is not repeated herein. Assuming the error ratio for the first detection is 0% (not reaching the error threshold of 50%), the error ratio for the second detection is 25% (not reaching the error threshold of 50%), and the error ratio for the third detection (the settlement result of the newest detection) is 50% (reaching the error threshold of 50%), it means that an abnormal situation of the target sensor X might have happened between the second detection and the third detection.

TABLE 1

| | the first satellite sensor | the second satellite sensor | the third satellite sensor | the fourth satellite sensor |
|---|---|---|---|---|
| the settlement result of the newest detection | 1 | 0 | 1 | 0 |

It can be known from the settlement result of the newest detection that, an abnormal situation might have happened to the target sensor X having the upstream-and-downstream relationship with the first satellite sensor to the fourth satellite sensor. Therefore, after replacing the target sensor X, the second computing device 12 may delete the detection result table corresponding to this target sensor X. In other words, each sensor may have a corresponding detection result table, and if the second computing device 12 determines, according to the detection result table, that an abnormal situation might happened to a sensor, it means said sensor should be removed or replaced with a new sensor. The second computing device 12 may delete or update the detection result table of the sensor having the abnormal situation, and the detection result tables of other sensors may also have some changes accordingly. Moreover, assuming the target sensor X is the first satellite sensor of another sensor, then when the target sensor X is removed, the record of the first satellite sensor in the detection result table of said another sensor is also removed.

Since the upstream-and-downstream relationship exists between the target sensor and the satellite sensor, through determining the correlation between the target sensor and the satellite sensor, time and cost required for examining the target sensor may be reduced, and at the same time, examination accuracy may be improved.

Please refer to FIG. 10a to FIG. 10e, wherein FIG. FIG. 10a to FIG. 10e are examples illustrating the method of building upstream-and-downstream configuration and method of anomaly detection for sensors according to an embodiment of the disclosure, wherein sensors in the examples shown in FIG. 10a to FIG. 10e are air quality sensors. Examples of FIG. 10b to FIG. 10e use the date of building the upstream-and-downstream relationship as the dividing point. That is, the method of building upstream-and-downstream configuration for sensors uses concentration of fine suspended particles obtained prior to building the upstream-and-downstream relationship as the target sensing data, and the method of anomaly detection of sensors uses concentration of fine suspended particles obtained after building the upstream-and-downstream relationship as the detection sensing data.

Figure 10A:
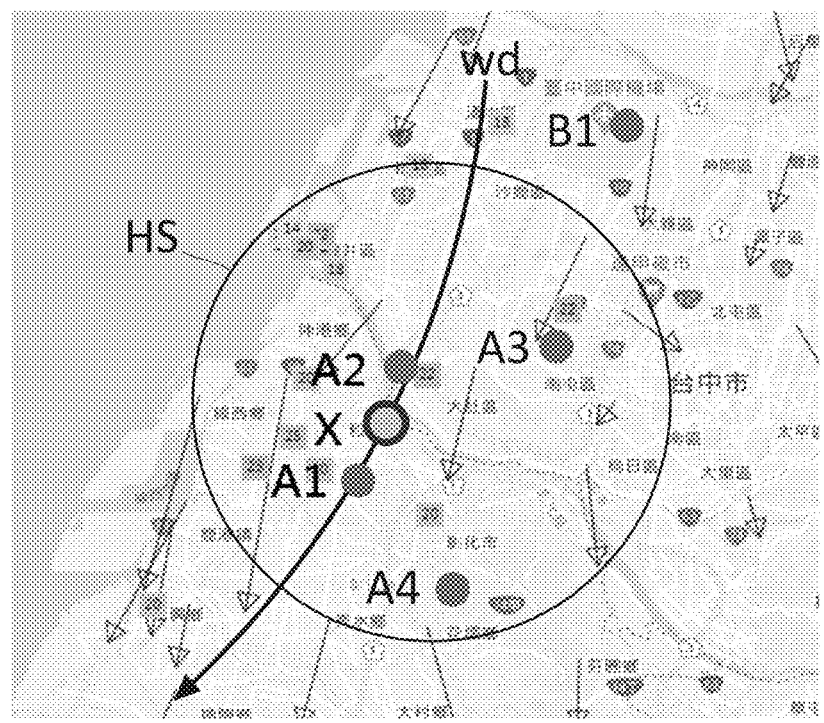
FIG. 10a to FIG. 10e are examples illustrating the method of building upstream-and-downstream configuration and method of anomaly detection for sensors according to an embodiment of the disclosure.
Figure 10B:
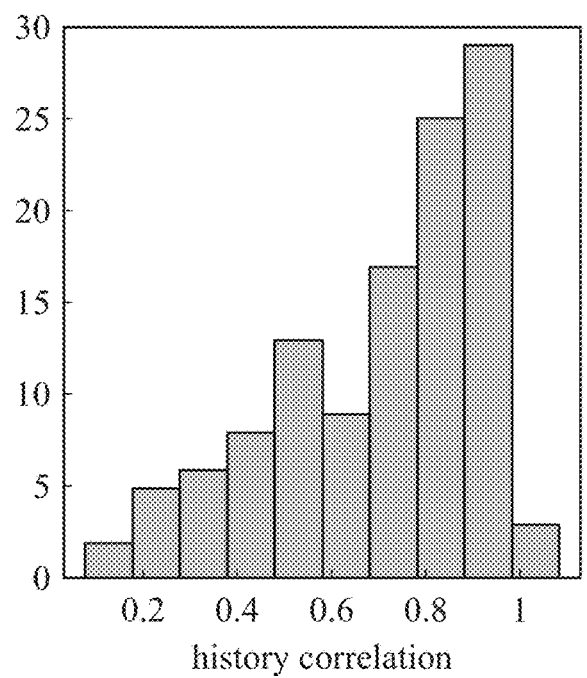
Figure 10C:
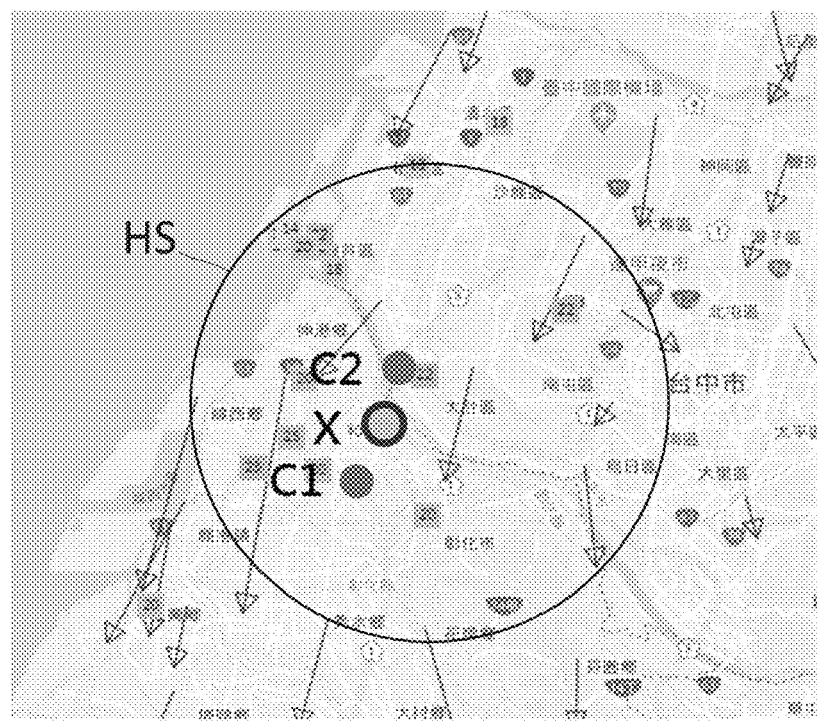
Figure 10D:
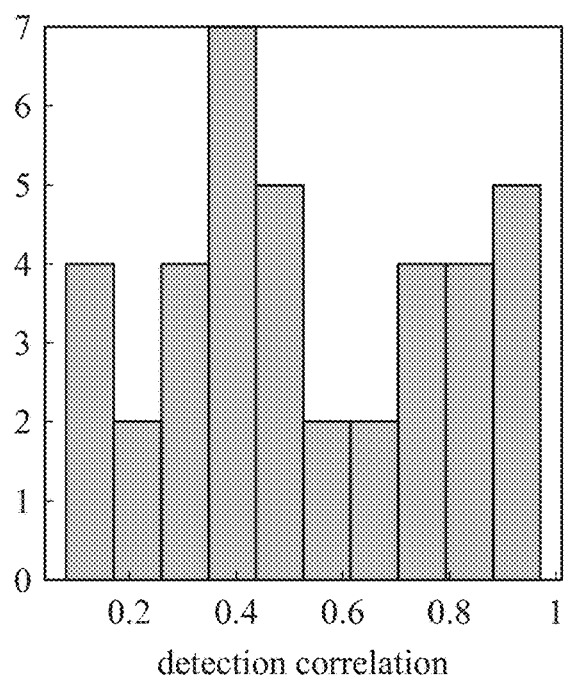

First, FIG. 10a shows the target sensor X and a number of sensors A1-A4 and B1. The computing device determines the hot zone sensors A1-A4 from the sensors A1-A4 and B1 are located in the hot zone HS, and uses each of the hot zone sensors A1-A4 as the candidate sensor. The computing device obtains four pieces of relative geographic location data between the target sensor X and the candidate sensors A1-A4 (step S11 of FIG. 2). The computing device performs the pollution determination algorithm according to the flow field data (wind field angle) wd, the pieces of relative geographic location data and a number of pieces of target sensing data of the target sensor X to obtain a number of pollution-associated periods (step S13 of FIG. 2), and calculates the correlations between a number of pieces of target sensing data of the target sensor X and a number of pieces of candidate sensing data of each of the candidate sensors A1-A4 to obtain a number of sensor correlations corresponding to each of the candidate sensors A1-A4 (step S15 of FIG. 2). Then, the computing device determines that the candidate sensors A1 and A2, whose quantity ratio of the sensor correlation being larger than or equal to the correlation threshold among the sensor correlations is larger than or equal to the default ratio, as the satellite sensors C1 and C2 of the target sensor. Take FIG. 10b as an example, wherein FIG. 10b shows the counting result of a number of sensor correlations corresponding to data obtained by the candidate sensor A1 prior to building the upstream-and-downstream relationship. The quantity ratio of the sensor correlations reaching the correlation threshold (0.6) is 71%, which reaches the default ratio (50%). Therefore, the computing device uses the candidate sensor A1 as the first satellite sensor C1 according to the counting result of FIG. 10b, same for the second satellite sensor C2, as shown in FIG. 10c. Then, by performing steps S231, S233 and S235 shown in FIG. 9, the computing device obtains the counting results of a number of detection correlations corresponding to the first satellite sensor C1 and the second satellite sensor C2, and sets the settlement results of the first satellite sensor C1 and the second satellite sensor C2 accordingly, as shown in table 2 below. FIG. 10d shows the counting result of the detection correlation of the first satellite sensor C1, wherein the quantity ratio of the detection correlations reaching the correlation threshold (0.6) is 38%, which does not reach the default ratio (50%). Therefore, the computing device sets the settlement result of the first satellite sensor C1 to 1 in table 2 below according to the counting result of FIG. 10d, and same for the second satellite sensor C2.

TABLE 2

|  | the first satellite sensor C1 | the second satellite sensor C2 |
| --- | --- | --- |
| the settlement result | 1 | 1 |

Then, the computing device performs step S25 of FIG. 9, to obtain a calculation of the error ratio being 100% according to the settlement results of the first satellite sensor C1 and the second satellite sensor C2 and a total number of the first satellite sensor C1 and the second satellite sensor C2, and performs step S27 of FIG. 9 determining that this error ratio reaches the error threshold (50%). Therefore, the computing device outputs the anomaly notification associated with the target sensor X. In short, the computing device determines that the target sensor X may have abnormal condition after the upstream-and-downstream relationship is built according to sensing data of the target sensor X, the first satellite sensor C1 and the second satellite sensor C2, and outputs the anomaly notification accordingly.

Figure 10E:
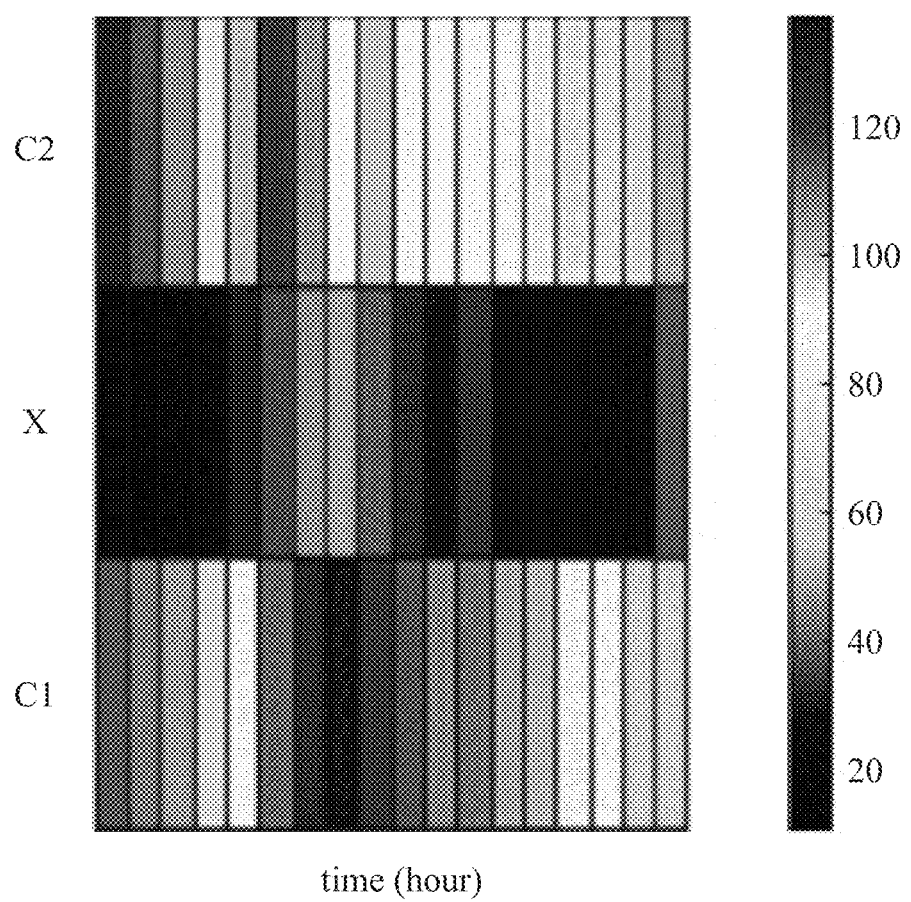

Please refer to FIG. 10e, which shows a number of actual sensing values obtained by the target sensor X, the first satellite sensor C1 and the second satellite sensor C2 during the detection pollution period after the upstream-and-downstream relationship is built, wherein different color depths represent different sensing values. Even though the target sensor X has the upstream-and-downstream relationship with both the first satellite sensor C1 and the second satellite sensor C2, but in FIG. 10e, color depths of the target sensor X and the first satellite sensor C1 vary greatly, and color depths of the target sensor X and the second satellite sensor C2 also vary greatly. It means that, the sensing result shown in FIG. 10e matches the settlement result shown in table 2 above.

In view of the above description, the method of building upstream-and-downstream configuration for sensors and the management system for sensors according to one or more embodiments of the disclosure may use the flow field data to build the upstream-and-downstream relationship, which is helpful in reducing cost for subsequent sensor detection (inspection). In addition, the method of anomaly detection of sensors and the management system for sensors according to one or more embodiments of the disclosure may perform detection (inspection) with only two sensors to realize self-inspection, without setting up a standard detection station or investing a lot of manpower, and effectively reduce the time, labor and cost of sensor inspection, thereby improving the inspection efficiency.

What is claimed is:

1. A method of building upstream-and-downstream configuration of sensors, performed by a computing device, comprising:

obtaining two pieces of geographic location data of a target sensor and a candidate sensor;

determining at least one pollution-associated period according to a plurality of pieces of flow field data corresponding to different time, the two pieces of geographic location data and a plurality of pieces of target sensing data obtained by the target sensor;

for each of the at least one pollution-associated period, calculating a correlation between the pieces of target sensing data obtained during the pollution-associated period and a plurality of pieces of candidate sensing data obtained during the pollution-associated period by the candidate sensor to obtain a plurality of sensor correlations corresponding to the pollution-associated period;

determining a quantity ratio of sensor correlations that are greater than or equal to a correlation threshold;

when the quantity ratio is greater than or equal to a default ratio, determining the candidate sensor has an upstream-and-downstream relationship with the target sensor, and storing upstream-and-downstream relationship information corresponding to the candidate sensor and the target sensor, wherein the upstream-and-downstream relationship information indicates the candidate sensor being a satellite sensor of the target sensor.

2. The method of building upstream-and-downstream configuration of sensors according to claim 1, wherein the computing device performs a pollution determination algorithm to determine the at least one pollution-associated period, and the pollution determination algorithm comprises:

selecting a plurality of pieces of pollution target sensing data that are greater than or equal to a pollution concentration upper limit from the pieces of target sensing data;

obtaining at least one pollution period corresponding to the pieces of pollution target sensing data; and for each of the at least one pollution period, determining whether the pollution period is the at least one pollution-associated period according to a correlation of a plurality of pieces of candidate flow field data corresponding to the pollution period among the pieces of flow field data and a relative geographic location between the target sensor and the candidate sensor.

3. The method of building upstream-and-downstream configuration of sensors according to claim 2, wherein the relative geographic location comprises a first direction from the target sensor to the candidate sensor and a second direction from the candidate sensor to the target sensor, and for each of the at least one pollution period, determining whether the pollution period is the at least one pollution-associated period according the correlation of the pieces of candidate flow field data corresponding to the pollution period among the pieces of flow field data and the relative geographic location comprises:

for each of the pieces of candidate flow field data, determining whether an included angle between a flow field direction of the candidate flow field data and the first direction or between the flow field direction and the second direction is smaller than or equal to an angle tolerance; and determining the pollution period is one of the at least one pollution-associated period when a determination result is positive.

4. The method of building upstream-and-downstream configuration of sensors according to claim 2, wherein obtaining the at least one pollution period corresponding to the pieces of pollution target sensing data comprises:

for each of the pieces of pollution target sensing data, performing:

using a time point of obtaining the pollution target sensing data as a reference time point;

obtaining a starting time point, wherein the starting time point is prior to the reference time point, and the target sensing data corresponding to the starting time point among the pieces of target sensing data is smaller than or equal to a pollution concentration lower limit;

obtaining an ending time point, wherein the ending time point is after the reference time point, and the target sensing data corresponding to the ending time point among the pieces of target sensing data is smaller than or equal to the pollution concentration lower limit; and using a period from the starting time point to the ending time point as one of the at least one pollution period.

5. The method of building upstream-and-downstream configuration of sensors according to claim 1, further comprising:

determining at least one hot zone sensor with a distance from the target sensor being smaller than a distance threshold; and using each of the at least one hot zone sensor as the candidate sensor.

6. The method of building upstream-and-downstream configuration of sensors according to claim 1, wherein the computing device further comprises an upstream-and-downstream configuration table corresponding to the target sensor, and the upstream-and-downstream configuration table is configured to store the upstream-and-downstream relationship information and comprises a device identification number of the target sensor and a device identification number of the satellite sensor of the target sensor.

7. The method of building upstream-and-downstream configuration of sensors according to claim 1, wherein the pieces of flow field data are a plurality of pieces of wind field data or a plurality of pieces of water flow field data.

8. A method of anomaly detection of sensors, performed by a computing device, comprising:

obtaining an upstream-and-downstream configuration table of a target sensor, wherein the upstream-and-downstream configuration table records the target sensor having upstream-and-downstream relationships with a plurality of satellite sensors;

for each of the satellite sensors, performing a pollution determination algorithm according to a plurality of pieces of detection flow field data, a plurality of pieces of geographic location data and a plurality of pieces of detection sensing data of the target sensor, to determine whether at least one detection pollution period exists, and when determining the at least one detection pollution period exists, performing:

for each of the at least one detection pollution period, calculating a correlation between a plurality of pieces of target detection data obtained by the target sensor in the detection pollution period and a plurality of pieces of satellite detection data obtained by the satellite sensor in the detection pollution period to obtain a plurality of detection correlations, determining a quantity ratio of detection correlations that are greater than or equal to a correlation threshold;

setting a settlement result as 1 when the quantity ratio is less than a default ratio, and setting a settlement result as 0 when the quantity ratio is greater than or equal to the default ratio;

calculating an error ratio according to the settlement results of the satellite sensors and a total number of the corresponding satellite sensors; and outputting an anomaly notification associated with the target sensor when the error ratio is greater than or equal to an error threshold.

9. A management system of sensors, comprising:

a storage device storing a plurality of pieces of target sensing data obtained by a target sensor, a plurality of pieces of candidate sensing data obtained by a candidate sensor and two pieces of geographic location data of the target sensor and the candidate sensor; and a computing device electrically connected to the storage device, and configured to perform a building upstream-and-downstream configuration procedure, comprising:

determining at least one pollution-associated period according to a plurality of pieces of flow field data, the two pieces of geographic location data and the pieces of target sensing data obtained by the target sensor;

for each of the at least one pollution-associated period, calculating a correlation between a plurality of pieces of target sensing data obtained by the target sensor during the pollution-associated period and a plurality of pieces of candidate sensing data obtained by the candidate sensor during the pollution-associated period to obtain a plurality of sensor correlations;

determining a quantity ratio of sensor correlations that are greater than or equal to a correlation threshold;

determining the candidate sensor has an upstream-and-downstream relationship with the target sensor when the quantity ratio is greater than or equal to a default ratio, and storing upstream-and-downstream relationship information corresponding to the candidate sensor and the target sensor, wherein the upstream-and-downstream relationship information indicates the candidate sensor being a satellite sensor of the target sensor.

10. The management system of sensors according to claim 9, wherein the computing device performs a pollution determination algorithm to determine the at least one pollution-associated period, and the pollution determination algorithm comprises:

selecting a plurality of pieces of pollution target sensing data that are greater than or equal to a pollution concentration upper limit from the pieces of target sensing data;

obtaining at least one pollution period corresponding to the pieces of pollution target sensing data; and for each of the at least one pollution period, determining whether the pollution period is the at least one pollution-associated period according to a correlation of a plurality of pieces of candidate flow field data corresponding to the pollution period among the pieces of flow field data and a relative geographic location between the target sensor and the candidate sensor.

11. The management system of sensors according to claim 10, wherein the relative geographic location comprises a first direction from the target sensor to the candidate sensor and a second direction from the candidate sensor to the target sensor, and for each of the at least one pollution period, the computing device determining whether the pollution period is one of the at least one pollution-associated period according to the correlation of the pieces of candidate flow field data corresponding to the pollution period among the pieces of flow field data and the relative geographic location comprises:

for each of the pieces of candidate flow field data, determining whether an included angle between a flow field direction of the candidate flow field data and the first direction or between the flow field direction and the second direction is smaller than or equal to an angle tolerance; and determining the pollution period is one of the at least one pollution-associated period when a determination result is positive.

12. The management system of sensors according to claim 10, wherein the computing device obtaining the at least one pollution period corresponding to the pieces of pollution target sensing data comprises:

for each of the pieces of pollution target sensing data, the computing device performing:

using a time point of obtaining the pollution target sensing data as a reference time point;

obtaining a starting time point, wherein the starting time point is prior to the reference time point, and the target sensing data corresponding to the starting time point among the pieces of target sensing data is smaller than or equal to a pollution concentration lower limit;

obtaining an ending time point, wherein the ending time point is after the reference time point, and the target sensing data corresponding to the ending time point among the pieces of target sensing data is smaller than or equal to the pollution concentration lower limit; and using a period from the starting time point to the ending time point as one of the at least one pollution period.

13. The management system of sensors according to claim 9, wherein the computing device is further configured to determine at least one hot zone sensor with a distance from the target sensor being smaller than a distance threshold, and use each of the at least one hot zone sensor as the candidate sensor.

14. The management system of sensors according to claim 9, wherein the computing device further comprises an upstream-and-downstream configuration table corresponding to the target sensor, and the upstream-and-downstream configuration table is configured to store the upstream-and-downstream relationship information and comprises a device identification number of the target sensor and a device identification number of the satellite sensor of the target sensor.

15. The management system of sensors according to claim 9, wherein the pieces of flow field data are a plurality of pieces of wind field data or a plurality of pieces of water flow field data.

16. The management system of sensors according to claim 9, wherein the computing device is further configured to perform the building upstream-and-downstream configuration procedure on each of a plurality of candidate sensors to obtain a plurality of satellite sensors of the target sensor, and, on each of the satellite sensors, perform:

performing a pollution determination algorithm according to a plurality of pieces of detection flow field data, the pieces of geographic location data and a plurality of pieces of detection sensing data of the target sensor, to determine whether at least one detection pollution period exists, and when determining the at least one detection pollution period exists, performing:
for each of the at least one detection pollution period, calculating a correlation between a plurality of pieces of target detection data obtained by the target sensor in the detection pollution period and a plurality of pieces of satellite detection data obtained by the satellite sensor in the detection pollution period to obtain a plurality of detection correlations,
determining a quantity ratio of detection correlations that are greater than or equal to a correlation threshold,
setting a settlement result as 1 when the quantity ratio is less than a default ratio, and
setting a settlement result as 0 when the quantity ratio is greater than or equal to the default ratio;
calculating an error ratio according to the settlement results of the satellite sensors and a total number of the corresponding satellite sensors; and
outputting an anomaly notification associated with the target sensor when the error ratio is greater than or equal to an error threshold.

17. The management system of sensors according to claim 9, wherein the computing device is a first computing device, and the first computing device is further configured to perform the building upstream-and-downstream configuration procedure on each of a plurality of candidate sensors to obtain a plurality of satellite sensors of the target sensor, and the management system of sensors further comprises:
a second computing device electrically connected to the storage device, and performing a pollution determination algorithm on each of the satellite sensors according to a plurality of pieces of detection flow field data, the pieces of geographic location data and a plurality of pieces of detection sensing data obtained by the target sensor, to determine whether at least one detection pollution period exists, and when determining the at least one detection pollution period exists performing:
for each of the at least one detection pollution period, calculating a correlation between a plurality of pieces of target detection data obtained by the target sensor in the detection pollution period and a plurality of pieces of satellite sensing data obtained by the satellite sensor in the detection pollution period to obtain a plurality of detection correlations,
determining a quantity ratio of detection correlations that are greater than or equal to a correlation threshold,
setting a settlement result as 1 when the quantity ratio is less than a default ratio, and
setting a settlement result as 0 when the quantity ratio is greater than or equal to the default ratio;
wherein the second computing device is further configured to perform:
calculating an error ratio according to the settlement results of the satellite sensors and a total number of the corresponding satellite sensors; and
outputting an anomaly notification associated with the target sensor when the error ratio is greater than or equal to an error threshold.

* * * * *